United States Patent
Park

(10) Patent No.: US 9,519,212 B2
(45) Date of Patent: Dec. 13, 2016

(54) MASK INSPECTION APPARATUS AND METHOD OF CONTROLLING THE SAME

(71) Applicant: Samsung Display Co., Ltd., Yongin, Gyeonggi-do (KR)

(72) Inventor: Hun-Jung Park, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 606 days.

(21) Appl. No.: 13/966,271

(22) Filed: Aug. 13, 2013

(65) Prior Publication Data
US 2014/0168410 A1    Jun. 19, 2014

(30) Foreign Application Priority Data

Dec. 14, 2012    (KR) .......................... 10-2012-0146638

(51) Int. Cl.
| | |
|---|---|
| H04N 5/232 | (2006.01) |
| G03F 1/84 | (2012.01) |
| G01N 21/94 | (2006.01) |
| G01N 21/956 | (2006.01) |

(52) U.S. Cl.
CPC .................. *G03F 1/84* (2013.01); *G01N 21/94* (2013.01); *G01N 21/956* (2013.01); *G01N 2021/95676* (2013.01)

(58) Field of Classification Search
None
See application file for complete search history.

(56) References Cited

U.S. PATENT DOCUMENTS

| H2114 H | * | 2/2005 | Novak | 356/124 |
|---|---|---|---|---|
| 8,224,590 B2 | | 7/2012 | Cho et al. | |
| 2004/0239950 A1 | * | 12/2004 | Mahon | G01B 11/24 356/606 |
| 2009/0244530 A1 | * | 10/2009 | Iida | G01N 21/95607 356/237.5 |
| 2012/0218455 A1 | * | 8/2012 | Imai | G02B 13/001 348/340 |

FOREIGN PATENT DOCUMENTS

| JP | 2004-338248 A | 12/2004 |
|---|---|---|
| KR | 10-1999-0054768 A | 7/1999 |
| KR | 10-2005-0073712 A | 7/2005 |
| KR | 10-2006-0041454 A | 5/2006 |
| KR | 10-2010-0099894 A | 9/2010 |
| KR | 10-2010-0131192 A | 12/2010 |

* cited by examiner

*Primary Examiner* — Sath V Perungavoor
*Assistant Examiner* — Janese Duley
(74) *Attorney, Agent, or Firm* — Lewis Roca Rothgerber Christie LLP

(57) ABSTRACT

A mask inspection apparatus includes a mask transfer unit configured to transfer a mask in one of a first direction and a direction opposite to the first direction, a displacement sensor unit configured to measure a distance to a sheet of the mask transferred by the mask transfer unit, a photographic unit configured to photograph the sheet of the mask transferred by the mask transfer unit, a control unit configured to send a height control signal for controlling a height of the photographic unit according to the measured distance, and a height control unit configured to control the height of the photographic unit according to the height control signal sent by the control unit.

17 Claims, 3 Drawing Sheets

MASK INSPECTION APPARATUS AND METHOD OF CONTROLLING THE SAME

CROSS-REFERENCE TO RELATED PATENT APPLICATION

This application claims priority to and the benefit of Korean Patent Application No. 10-2012-0146638, filed in the Korean Intellectual Property Office on Dec. 14, 2012, the entire disclosure of which is incorporated herein by reference.

BACKGROUND

1. Field

The present invention relates to a mask inspection apparatus and a method of controlling the same.

2. Description of the Related Art

Recently, there have been increased expectations for organic light emitting diode (OLED) displays, requiring attention to various apparatuses used in the manufacturing process, and requiring control of quality during the process. Particularly, masks used for forming organic materials of OLED displays are highly defined in view of the high resolution of displays.

However, when manufacturing OLED displays by using highly defined masks, if impurities exist on mask sheets or mask sheets are damaged, defect rates of displays may be increased. However, in general, mask inspection apparatuses and general methods of controlling the same are not well developed, as masks are inspected by using fixed cameras, thereby making it difficult or impossible to precisely inspect whether there are detects in the masks.

SUMMARY

Aspects of embodiments of the present invention include a mask inspection apparatus capable of inspecting a mask regardless of kind or in spite of a sag of a sheet of the mask, and a method of controlling the mask inspection apparatus. However, this aspect is merely exemplary, and the scope of the present invention is not limited thereto.

According to an aspect of the present invention, a mask inspection apparatus includes a mask transfer unit configured to transfer a mask in one of a first direction and a direction opposite to the first direction; a displacement sensor unit configured to measure a distance to a sheet of the mask transferred by the mask transfer unit; a photographic unit configured to photograph the sheet of the mask transferred by the mask transfer unit; a control unit configured to send a height control signal according to the distance measured by the displacement sensor unit; and a height control unit configured to control the height of the photographic unit according to the height control signal sent by the control unit.

The mask transfer unit may be configured to transfer the mask in the first direction under the displacement sensor unit and then to the photographic unit. The control unit may be configured to continuously send the height control signal for the photographic unit according to the distance measured by the displacement sensor unit, and the height control unit may be configured to continuously control the height of the photographic unit according to the height control signal.

The control unit may be configured to send the height control signal to control a distance from an area of the sheet of the mask photographed by the photographic unit to the photographic unit within a set range.

The mask inspection apparatus may further include a first position control unit configured to control a position of the displacement sensor unit in one of a second direction and a direction opposite to the second direction, the second direction intersecting the direction in which the height control unit controls the height of the photographic unit and intersecting the first direction.

The displacement sensor unit may include a plurality of displacement sensors separate from one another in a second direction, the second direction intersecting the direction in which the height control unit controls the height of the photographic unit and intersecting the first direction. The mask inspection apparatus may further include a second position control unit configured to control a position of the photographic unit in one of the second direction and a direction opposite to the second direction. The mask transfer unit may be configured to transfer the mask in the first direction under the displacement sensor unit and then to the photographic unit. After the mask transfer unit transfers the mask in the first direction, the control unit may be configured to send a position adjustment signal for adjusting the position of the photographic unit in one of the second direction and the direction opposite to the second direction, and the second position control unit may control the position of the photographic unit in one of the second direction and the direction opposite to the second direction, and after the second position control unit controls the position of the photographic unit, the mask transfer unit may be configured to transfer the mask in the direction opposite to the first direction, and while the mask transfer unit is transferring the mask in the direction opposite to the first direction, the control unit may be configured to send the height control signal to control the height of the photographic unit according to the height control signal sent by the control unit.

The photographic unit may include a plurality of cameras separate from one another in a second direction, the second direction intersecting the direction in which the height control unit controls the height of the photographic unit and intersects the first direction. The control unit may be configured to send height control signals for controlling a height of each of the plurality of cameras, and the height control unit may be configured to control the height of each of the plurality of cameras.

According to an aspect of the present invention, a method of controlling a mask inspection apparatus includes transferring a mask in a first direction; measuring a distance from a displacement sensor unit to a sheet of the mask; controlling a height of a photographic unit; and photographing the sheet of the mask according to the measured distance.

The transferring the mask in the first direction may include transferring the mask under the displacement sensor unit and to the photographic unit. In the transferring a mask in the first direction, the height of the photographic unit may be continuously controlled according to the measured distance continuously obtained by the displacement sensor unit. The height of the photographic unit may be controlled so that a distance from an area of the sheet of the mask photographed by the photographic unit to the photographic unit is controlled within a set range.

In the measuring a distance from a displacement sensor unit to a sheet of the mask, the distance from the displacement sensor unit to the sheet of the mask may be obtained in a plurality of areas separate from one another in a second direction, the second direction intersecting a direction for controlling the height of the photographic unit and intersecting the first direction.

The transferring the mask in the first direction may include transferring the mask under the displacement sensor unit and to the photographic unit, and the method may further include controlling a position of the photographic unit in one of a second direction and a direction opposite to the second direction, the second direction intersecting the direction for controlling the height of the photographic unit and intersecting the first direction; and transferring the mask in a direction opposite to the first direction, controlling the height of the photographic unit according to the measured distance.

The photographic unit may include a plurality of cameras separate from one another in a second direction, the second direction intersecting the direction for controlling the height of the photographic unit and intersecting the first direction, and the method may further include controlling the height of each of the plurality of cameras.

BRIEF DESCRIPTION OF THE DRAWINGS

The above and other features and aspects of the present invention will become more apparent by describing in detail exemplary embodiments thereof with reference to the attached drawings in which.

DETAILED DESCRIPTION

Figure 1:
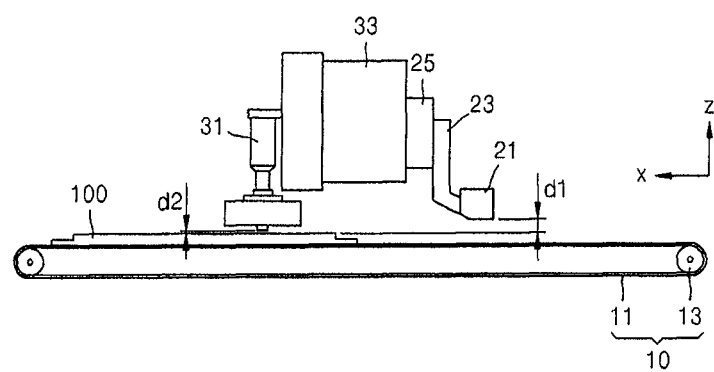
FIG. 1 is a schematic side view illustrating a mask inspection apparatus according to an embodiment of the present invention.

Hereinafter, the present invention will be described more fully with reference to the accompanying drawings, in which embodiments of the invention are shown. The invention may, however, be embodied in many different forms and should not be construed as being limited to the embodiments set forth herein. Rather, these embodiments are provided so that this disclosure is thorough and conveys aspects of the invention to those skilled in the art. In the drawings, the thicknesses of layers and regions may be exaggerated or contracted for convenience of description.

In the following embodiments, an x-axis, a y-axis, and a z-axis are limited to three axes on an orthogonal coordinate system, but it may be understood as a broader meaning including the same. For example, the x-axis, the y-axis, and z-axis may be orthogonal to one another but may indicate different directions that are not orthogonal to one another.

As used herein, the term "and/or" includes any and all combinations of one or more of the associated listed items.

FIG. 1 is a schematic side view illustrating a mask inspection apparatus according to an embodiment of the present invention.

As illustrated, the mask inspection apparatus according to the present embodiment includes a mask transfer unit 10, a displacement sensor unit, a photographic unit, a control unit, and a height-control unit.

The mask transfer unit 10 may transfer a mask 100 in one of a first direction that is a +x direction and a direction opposite to the first direction, which is a −x direction. In the drawing, the mask transfer unit 10 is shown to include a conveyer belt 11 and a roller 13 rotating the conveyer belt 11, but it is not limited thereto and may be changed and, for example, include a rail extending along an x-axis and a carrier formed in the shape of a plate with rollers moving on the rail.

The displacement sensor unit may include a displacement sensor 21 as shown in FIG. 1. The displacement sensor unit may obtain information related to a distance to a sheet of the mask 100 transferred by the mask transfer unit 10. For example, it is possible to obtain information related to a distance d1 from a bottom of the displacement sensor 21 to the sheet of the mask 100. The displacement sensor 21, for example, may obtain the information related to the distance d1 from the bottom of the displacement sensor 21 to the sheet of the mask 100 by emitting a laser beam to the sheet of the mask 100 and sensing the laser beam reflected to the displacement sensor 21.

In this case, the mask 100 may include a frame with a tetragonal opening thereinside. The sheet may be coupled with the frame by welding or the like to shield the opening. The sheet may have a single aperture or a plurality of apertures through which evaporation materials pass. In this case, generally, a mask designates a sheet. However, the mask 100 may be considered a mask frame assembly formed of the mask (i.e., the sheet) and a frame coupled to each other. Hereinafter, for convenience, the mask 100 will be described as having a frame with a tetragonal opening thereinside and a sheet coupled with the frame.

The photographic unit, as shown in the drawing, may include a camera 31. The photographic unit photographs the sheet of the mask 100 transferred by the mask transfer unit 10, thereby inspecting whether there are impurities on the sheet and/or whether the sheet is damaged. The camera 31 may be a charge-coupled device (CCD), a complementary metal-oxide semiconductor (CMOS), or the like.

The control unit (not shown) may output a height control signal to control a height of the photographic unit from the sheet of the mask 100 in a +z direction according to the distance-related information obtained by the displacement sensor unit.

When the height control signal is transferred to the height control unit 33, the height control unit 33 may control a height of the photographic unit, that is, the camera 31 in the +z direction according to a corresponding signal. This may be understood as controlling a distance d2 between the camera 31 and the sheet of the mask 100.

The displacement sensor unit, the photographic unit, and the height control unit 33 may be supported by a frame (not shown) or the like.

Figure 2:
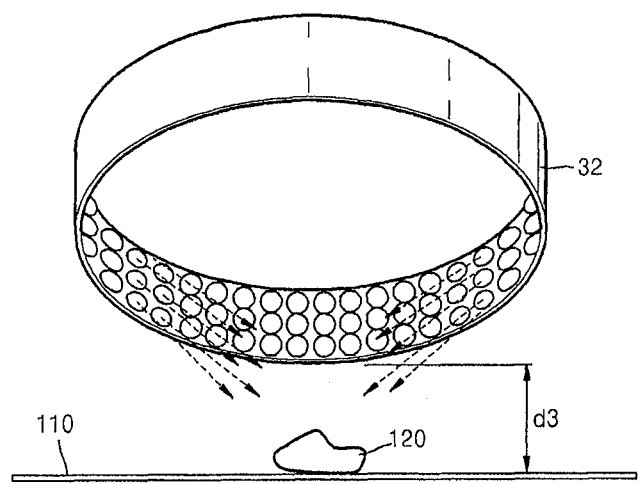
FIGS. 2 and 3 are views illustrating a part of a photographic unit and a part of a mask sheet.
Figure 3:
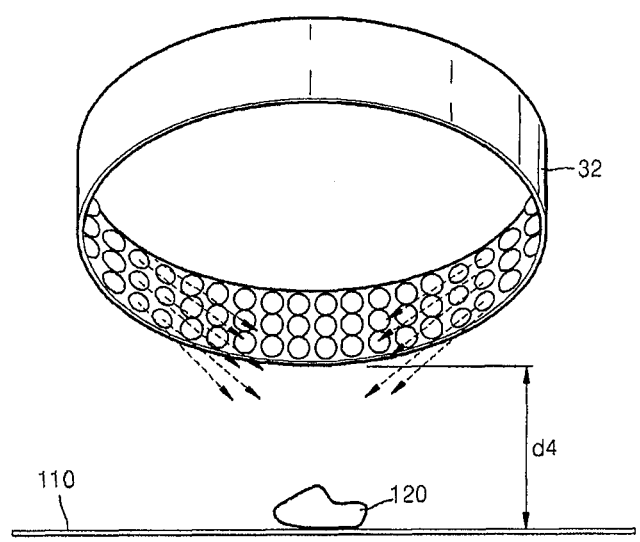

FIGS. 2 and 3 are schematic views illustrating a part of the photographic unit of the mask inspection apparatus and a part of a sheet 110 of the mask 100. As shown in the drawings, the photographic unit of the mask inspection apparatus may include a lighting unit 32 with light sources such as light emitting diodes (LED) formed thereon on an end that emit light in a direction of the sheet 10 of the mask 100. The light unit 32 emits light to a part to be inspected by the camera 31 of the photographic unit to allow the photographic unit to obtain information related to the sheet 110 of the mask 100 with sufficient light.

As shown in FIGS. 2 and 3, distances between the bottom of the camera 31 of the photographic unit and the sheet 110 of the mask 100 are different, such as d3 and d4. However, regardless of the distances, d3 and d4, between the bottom of the camera 31 of the photographic unit and the sheet 110 of the mask 100, the lighting unit 32 emits a certain or set amount of light to the sheet 110 of the mask 100. Accordingly, if there is present an impurity 120 on the sheet 10 of the mask 100, a reflecting angle at the impurity 120 varies depending on the distances d3 and d4 between the bottom of the camera 31 of the photographic unit and the sheet 110 of the mask 100 in such a way that inspection parameters obtained by the camera 31 of the photographic unit vary though the same shaped and sized impurity 120 is present, thereby deteriorating inspection ability of mask inspection apparatuses.

However, in case of the mask inspection apparatus according to the present embodiment, as described above, the displacement sensor 21 of the displacement sensor unit obtains distance-related information related to distance to the sheet of the mask 100, the control unit outputs a height control signal to control a height from the sheet to the photographic unit in the +z direction according to the distance-related information obtained by the displacement sensor unit, and according thereto, the height control unit 33 controls a height of the photographic unit. That is, the height control unit 33 controls the height of the camera 31 in the +z direction in such a way that a distance from a spot (or area) of the sheet, photographed by the photographic unit, to the photographic unit is controlled within a previously determined or set range. Accordingly, the mask inspection apparatus may obtain accurate information related to the impurity on the sheet 110 of the mask 100 to allow the mask 100 to be smoothly maintained.

Particularly, as display apparatuses have become larger, the mask 110 has also become larger. To manufacture a plurality of display apparatuses at the same time on one mother glass, the mask 100 is typically enlarged. As the mask 100 has become large, a center of the sheet 110 may sag due to its own weight in the −z direction, that is, the direction in which gravity acts. As a result of this, the center of the sheet 110 of the mask 100 may sag in a range of about 120 μm to about 450 μm, relative to parts adjacent to the frame. However, general photographic units included in mask inspection apparatuses generally only obtain accurate information related to impurities, based on areas where focusing is performed, within ranges of less than 50 μm upwardly, that is, in the +z direction, and downwardly, that is, in the −z direction, respectively. Accordingly, when fixing a height of the photographic unit, it is difficult or impossible to precisely inspect the whole area of the sheet 110 of the mask 100.

However, when the mask inspection apparatus according the present embodiment is used, as described above, the displacement sensor 21 of the displacement sensor unit obtains information related to the distance to the sheet of the mask 100 and the height control unit 33 controls the height of the photographic unit (that is, the height of the camera 31 is controlled in the +z direction according to the distance information) so that the distance between the area of the sheet 110 of the mask 100 to be photographed by the photographic unit is within a previously determined or set range. Accordingly, the mask inspection apparatus according to the present embodiment obtains accurate information related to an impurity on the sheet 110 of the mask 100, to allow the mask 100 to be smoothly maintained.

When inspecting a mask, while the mask transfer unit 10 transfers the mask 100 in the first direction that is the +x direction, the transferred mask 100, as shown in FIG. 1, may pass under the displacement sensor 21 of the displacement sensor unit and approach the camera 31 of the photographic unit. Accordingly, it is possible to continuously transfer the mask 100 in the first direction, that is the +x direction, in such a way that the sheet 110 of the mask 100 may be precisely inspected by the camera 31 of the photographic unit.

That is, while the mask transfer unit 10 transfers the mask 100 in the first direction that is the +x direction, the control unit may continuously output the height control signal for the camera 31 of the photographic unit according to distance-related information continuously obtained by the displacement sensor 21 of the displacement sensor unit. The height control unit 33 may continuously control the height of the camera 31 of the photographic unit in the +z direction according to the height control signal. As such, while inspecting the sheet 110 of the mask, a transfer of the mask 100 does not stop and the sheet 110 of the mask 100 is continually inspected, thereby quickly and accurately inspecting the mask 100.

The mask inspection apparatus may further include a first position control unit 25. The first position control unit 25 may control a position of the displacement sensor unit, that is, a position of the displacement sensor 21 in a second direction (+y direction) or in a direction opposite to the second direction. Here, the second direction (+y direction) may intersect both a direction (+z direction) in which the height control unit 33 controls the height of the camera 31 of the photographic unit and the first direction that is the +x direction. The first direction, the second direction, and the direction in which the height control unit 33 controls the height of the camera 31 of the photographic unit may be orthogonal to one another. As shown in FIG. 1, the displacement sensor 21 may be connected to the first position control unit 25 by a sensor supporting unit 23. In such a configuration, the first position control unit 25 controls a position of the sensor supporting unit 23 in one of the second direction, that is the +y direction, and the −y direction opposite to the second direction.

The first position control unit 25 controls the position of the sensor supporting unit 23 in one of the second direction, that is +y direction, and the −y direction opposite to the second direction, so that the displacement sensor unit may obtain information related to the distance to the sheet 110 of the mask 100 corresponding to a part to be inspected by the camera 31 of the photographic unit (among areas of the sheet 110 of the mask 100).

In some embodiments, when the photographic unit includes a plurality of cameras, for example, two cameras, the first position control unit 25 may control the position of the displacement sensor 21 in such a way that the mask transfer unit 10 transfers the mask 100 in the first direction (that is the +x direction) and one displacement sensor 21 is moved to different parts of the sheet 110 of the mask 100 that are to be inspected by the two cameras of the photographic unit. As such, the displacement sensor 21 alternately obtains information related to distances to the sheet 110 at corresponding parts. In this way, when the photographic unit includes two cameras, it is possible to allow distances from the respective cameras to parts of the sheet 110 to be photographed by corresponding cameras to be within a previously determined or set range. Using the displacement sensor 21, the control unit outputs height control signals to control respective heights of the plurality of cameras, and the height control unit 33 individually controls the respective heights of the plurality of cameras.

A mask inspection apparatus according to another embodiment of the present invention may further include a second position control unit capable of controlling positions of respective cameras of a plurality of cameras of the photographic unit in one of the second direction, that is the +y direction, and the −y direction opposite to the second direction. The second position control unit, for example, may be formed together with the height control unit 33 in a single body or may be an additional control unit different from the height control unit 33. The second position control unit may control the position of the photographic unit by receiving a position adjustment signal outputted by the control unit, and thereby adjust the position of respective cameras in one of the second direction that is the +y direction and the −y direction opposite to the second direction.

The mask transfer unit 10 transfers the mask 100 in the first direction, that is the +x direction, to allow the transferred mask 100 to pass under the displacement sensor unit, including a displacement sensor 21. As the transferred mask is passed under the displacement sensor unit, the first position control unit 25 controls the displacement sensor 21 to be alternately located in two areas separate from each other in the second direction, that is the +y direction, and therefore to alternately obtain information related to distances from the corresponding areas of the sheet 110 of the mask. Then, the transferred mask is passed under the photographic unit (including one camera 31).

A height of the camera 31 of the photographic unit in the +z direction is controlled by the height control unit 33 in an area corresponding to one of the two areas to perform an inspection of the sheet 110. The position of the camera 31 of the photographic unit is then adjusted to an area corresponding to the other of the two areas. Then, the mask transfer unit 10 transfers the mask 100 in the −x direction opposite to the first direction to perform an inspection of the mask 100 in the other of the two areas. A height of the camera 31 of the photographic unit in the other area may be controlled by the height control unit 33 by using the information related to the distance to the sheet 110 of the mask obtained by the displacement sensor 21 of the displacement sensor unit in the other two areas when the mask 100 was initially transferred in the first direction that is the +x direction.

Using the configuration described above, when the mask transfer unit 10 transfers the mask 100 in the −x direction opposite to the first direction, in addition to the first direction, a distance between the photographic unit and the sheet 110 of the mask 100 may be controlled within a previously determined or set range to precisely and quickly perform a mask inspection at the other areas.

Figure 4:
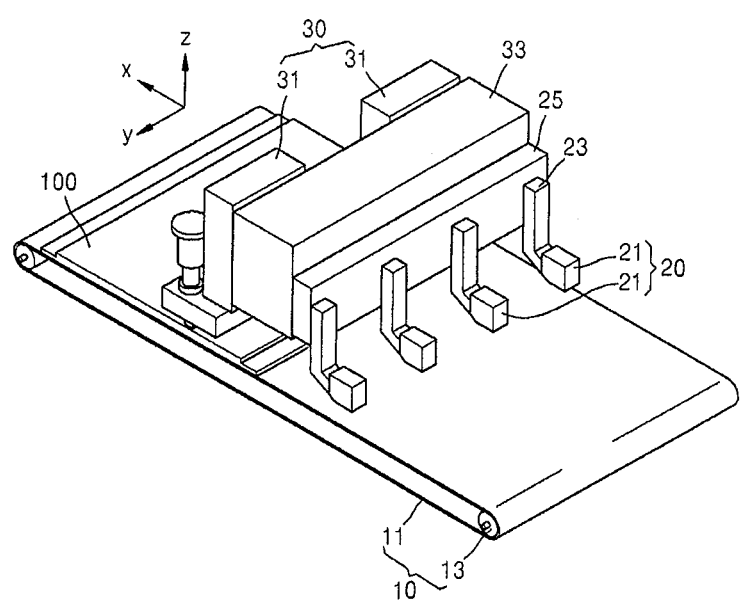
FIG. 4 is a schematic perspective view illustrating a mask inspection apparatus according to another embodiment of the present invention.

FIG. 4 is a perspective view schematically illustrating a mask inspection apparatus according to another embodiment of the present invention. In the mask inspection apparatus according to the present embodiment, a displacement sensor unit 20 includes a plurality of displacement sensors 21 disposed separate from one another in the second direction, that is the +y direction. In the drawing, there the displacement sensor unit 20 includes four displacement sensors 21, however, it is not limited thereto. In addition, a photographic unit 30 also includes a plurality of cameras 31 disposed separate from one another in the second direction, that is the +y direction. The number of cameras 31 may be less than the number of the displacement sensors 21, and in the drawing, the photographic unit 30 includes two cameras 31, however, the number of cameras is not limited thereto.

In the mask inspection apparatus according to the present embodiment, the mask transfer unit 10 transfers the mask 100 in the first direction, that is the +x direction, so that the transferred mask 100 passes under the displacement sensor unit 20 including the four displacement sensors 21 and approaches the photographic unit 30 including the two cameras 31. The four displacement sensors 21 separate from one another in the second direction, that is the +y direction, obtain information related to distances to the sheet 110 of the mask 100 at respective areas (e.g., spots). Heights of the two cameras 31 of the photographic unit 30 in the +z direction may be controlled by the height control unit 33 in areas corresponding to a first area and a second area where two of the four displacement sensors 21 are located, respectively, to perform an inspection on the sheet 110 of the mask 100.

After that, the transfer of the mask 100 in the first direction is finished and the inspection on the mask 100 in the areas corresponding to the first area and the second area is finished. Then, positions of the cameras 31 of the photographic unit 30 are controlled by the second position control unit to areas corresponding to a third area and a fourth area, where two other displacement sensors 21 of the four displacement sensors 21 were located. Then, the mask transfer unit 10 transfers the mask 100 in the −x direction opposite to the first direction to perform an inspection on the mask 100. In this case, heights of the cameras in the third area and the fourth area may be controlled by the height control unit 33 by using information related to distances to the sheet 110 of the mask 100 previously obtained by the two displacement sensors 21 in the third area and the fourth area while initially transferring the mask 100 in the first direction.

Using the configuration described above, when the mask transfer unit 10 transfers the mask 100 the −x direction opposite to the first direction, in addition to the first direction, the distance between the photographic unit 30 and the sheet 110 of the mask 100 may be controlled within a previously determined or set range to precisely and quickly perform a mask inspection of the third area and the fourth area.

As described above, when manufacturing a small display apparatus, it is possible to manufacture a plurality of display apparatuses on one mother glass at the same time. In this case, each area on the one mother glass, which will become a small display apparatus, may be designated as a cell. In the mask inspection apparatuses according to the described embodiments and variations thereof, when a displacement sensor of a displacement sensor unit obtains distance-related information for changing a position of the photographic unit in a second direction (or a plurality of displacement sensors of a displacement sensor unit separate from one another in the second direction) in corresponding areas, the distance-related information may correspond to each cell.

The mask inspection apparatuses according the embodiments of the present invention have been described, but the present invention is not limited thereto. Various embodiments and variations thereof, such a method of controlling the mask inspection apparatuses or the like, may be included therein.

In a method of controlling the mask inspection apparatus according to an embodiment of the present invention, referring to FIG. 1, the mask 100 is transferred in the first direction (that is the +x direction) and information related to the distance d1 from the displacement sensor unit to the sheet of the mask 100 is obtained by the displacement sensor 21, and the height of the photographic unit inspecting the sheet of the mask 100 is thereby controlled. In this case, while transferring the mask 100 in the first direction (that is the +x direction), the transferred mask 100 may pass under the displacement sensor unit and then approach the photographic unit. When transferring the mask 100 in the first direction (that is the +x direction), the height of the photographic unit is controlled according to the distance-related information obtained by the displacement unit so that the distance from the area of the sheet of the mask 100 photographed by the photographic unit to the photographic unit is within a previously determined or set range.

When obtaining the information related to the distance to the sheet of the mask by the displacement sensor unit, the displacement sensor unit may obtain (e.g., be controlled to obtain) information related to a distance from the displacement sensor unit to the sheet of the mask 100 in each of a plurality of areas separate from one another in the second direction (that is the +y direction). The second direction (that is the +y direction) intersects both the direction for controlling the height of the photographic unit (which is the +z direction) and the first direction (that is the +x direction).

Similar to the mask inspection apparatus as described above, in the method of controlling the mask inspection apparatus, the mask 100 is transferred in the first direction (that is the +x direction) to pass under the displacement sensor unit and then approach the photographic unit, in which the sheet of the mask 100 is inspected. The height of the photographic unit is controlled according to the distance-related information obtained by the displacement sensor unit while transferring the mask in the first direction. After that, the position of the photographic unit may be controlled in one of the second direction which is +y direction and the direction opposite to the second direction. After that, the mask 100 is transferred in the −x direction opposite to the first direction and the sheet of the mask 100 is inspected. The height of the photographic unit in this area is controlled according to the previously obtained distance-related information. The displacement sensor unit may change position in the second direction and obtain distance-related information at different positions or may include a plurality of displacement sensors to obtain distance-related information at different positions.

The photographic unit of the mask inspection apparatus includes a plurality of cameras disposed separate from one another in the second direction (that is the +y direction).

As described above, when manufacturing a small display apparatus, it is possible to manufacture a plurality of display apparatuses on one mother glass at the same time. In this case, each area on the one mother glass, which will become a small display apparatus, may be designated as a cell. In the method of controlling the mask inspection apparatuses according to described embodiments and variations thereof, a displacement sensor of a displacement sensor unit may obtain distance-related information by changing a position of displacement sensors of a displacement sensor unit in a second direction (that is a +y direction), or by using a plurality of displacement sensors separately disposed in the +y direction. Thereby, distance-related information may be identified for each cell.

While the present invention has been particularly shown and described with reference to exemplary embodiments thereof, it will be understood by those of ordinary skill in the art that various changes in form and details may be made without departing from the spirit and scope of the present invention as defined by the following claims and equivalents thereof.

What is claimed is:

1. A mask inspection apparatus comprising:
a mask transfer unit comprising at least one of a conveyor or a carrier to transfer a mask in one of a first direction and a direction opposite to the first direction;
a displacement sensor unit comprising a displacement sensor, the displacement sensor unit being arranged above the conveyor or the carrier to measure a distance from the displacement sensor to an upper surface of a sheet of the mask transferred by the mask transfer unit; and
a photographic unit comprising a camera, the camera being arranged above the conveyor or the carrier to photograph the upper surface of the sheet of the mask transferred by the mask transfer unit, a height of the photographic unit being controllable according to the distance measured by the displacement sensor.

2. The apparatus of claim 1, wherein the at least one of the conveyor or the carrier is configured to transfer the mask in the first direction under the displacement sensor unit and then to the photographic unit.

3. The apparatus of claim 2, wherein the height of the photographic unit is continuously controllable according to the distance measured by the displacement sensor when the mask transfer unit transfers the mask in the first direction.

4. The apparatus of claim 3, wherein a distance from an area of the sheet of the mask photographed by the camera to the photographic unit is controllable within a set range.

5. The apparatus of claim 1, wherein a position of the displacement sensor unit in one of a second direction and a direction opposite to the second direction is controllable, the second direction intersecting a direction in which the height of the photographic unit is controllable and intersecting the first direction.

6. The apparatus of claim 1, wherein the displacement sensor unit comprises a plurality of displacement sensors separate from one another in a second direction, the second direction intersecting a direction in which the height of the photographic unit is controllable and intersecting the first direction.

7. The apparatus of claim 6, wherein a position of the photographic unit in one of the second direction and a direction opposite to the second direction is controllable.

8. The apparatus of claim 7, wherein the height of the photographic unit is continuously controllable according to the distance measured by the displacement sensor when the mask transfer unit transfers the mask in the first direction,
wherein, the at least one of the conveyor or the carrier is configured to transfer the mask in the first direction under the displacement sensor unit and then to the photographic unit,
wherein, after the mask transfer unit transfers the mask in the first direction, the position of the photographic unit in one of the second direction and the direction opposite to the second direction is controllable, and
wherein, while the mask transfer unit is transferring the mask in the direction opposite to the first direction, the height of the photographic unit is controllable.

9. The apparatus of claim 1, wherein the photographic unit comprises a plurality of cameras separate from one another in a second direction, the second direction intersecting a direction in which the height of the photographic unit is controllable and intersects the first direction.

10. The apparatus of claim 9, wherein a height of each of the plurality of cameras is controllable.

11. A method of controlling a mask inspection apparatus to manufacture a display, the method comprising:
transferring a mask in a first direction using at least one of a conveyor or a carrier;
measuring a distance from a displacement sensor of a displacement sensor unit to an upper surface of a sheet of the mask, wherein the displacement sensor is arranged above the conveyor or the carrier;
controlling a height of a photographic unit according to the measured distance; and
photographing the sheet of the mask using a camera of the photographic unit, wherein the camera is arranged above the conveyor or the carrier to photograph the upper surface of the sheet of the mask.

12. The method of claim 11, wherein, the transferring the mask in the first direction comprises transferring the mask under the displacement sensor unit and to the photographic unit.

13. The method of claim 12, wherein, in the transferring a mask in the first direction, the height of the photographic unit is continuously controlled according to the measured distance continuously obtained by the displacement sensor unit.

14. The method of claim 12, wherein the height of the photographic unit is controlled so that a distance from an area of the sheet of the mask photographed by the photographic unit to the photographic unit is controlled within a set range.

15. The method of claim 11, wherein, in the measuring the distance from a displacement sensor to an upper surface of a sheet of the mask, the distance from the displacement sensor to the upper surface of the sheet of the mask is obtained in a plurality of areas separate from one another in a second direction, the second direction intersecting a direction for controlling the height of the photographic unit and intersecting the first direction.

16. The method of claim 11, wherein the transferring the mask in the first direction comprises transferring the mask under the displacement sensor unit and to the photographic unit, the method further comprising:
controlling a position of the photographic unit in one of a second direction and a direction opposite to the second direction, the second direction intersecting the direction for controlling the height of the photographic unit and intersecting the first direction; and
transferring the mask in a direction opposite to the first direction, controlling the height of the photographic unit according to the measured distance.

17. The method of claim 11, wherein the photographic unit comprises a plurality of cameras separate from one another in a second direction, the second direction intersecting the direction for controlling the height of the photographic unit and intersecting the first direction, wherein the method further comprises:
controlling the height of each of the plurality of cameras.

* * * * *